United States Patent [19]

Levander et al.

[11] Patent Number: 5,454,793
[45] Date of Patent: Oct. 3, 1995

[54] MEDICINE DISPENSING DEVICE

[75] Inventors: Gustav Levander, Bromma; Olle Ljungquist, Täby, both of Sweden

[73] Assignee: Pharmacia Aktiebolag, Stockholm, Sweden

[21] Appl. No.: 108,638

[22] PCT Filed: Jan. 14, 1993

[86] PCT No.: PCT/SE93/00015

§ 371 Date: Aug. 30, 1993

§ 102(e) Date: Aug. 30, 1993

[87] PCT Pub. No.: WO93/14799

PCT Pub. Date: Aug. 5, 1993

[30] Foreign Application Priority Data

Jan. 22, 1992 [SE] Sweden .................................. 9200172

[51] Int. Cl.⁶ ........................................................ A61M 5/00
[52] U.S. Cl. ............................ 604/235; 604/207; 604/233
[58] Field of Search ...................................... 604/207–208, 604/211, 218, 224, 232–235

[56] References Cited

U.S. PATENT DOCUMENTS

| | | | |
|---|---|---|---|
| 2,118,221 | 5/1938 | Montuori | 128/218 |
| 4,592,745 | 6/1986 | Rex et al. | 604/211 |
| 5,098,382 | 3/1992 | Haber et al. | 604/110 |

FOREIGN PATENT DOCUMENTS

| | | | |
|---|---|---|---|
| 236317 | 5/1960 | Australia | 604/235 |
| 0298067 | 2/1989 | European Pat. Off. | |
| 2613789 | 10/1987 | France. | |
| 132836 | 6/1964 | New Zealand. | |
| 227895 | 3/1991 | New Zealand. | |
| 379089 | 9/1975 | Sweden. | |
| 1369594 | 9/1974 | United Kingdom. | |

Primary Examiner—Corrine M. Maglione
Attorney, Agent, or Firm—Pollock, Vande Sande & Priddy

[57] ABSTRACT

A medicine dispensing device including a slotted housing, a front end, a rear end, at least one threaded portion in the vicinity of the rear end, a dosage ampoule fitting in the vicinity of the front end and a discharge conduit for connection with a discharge ampoule. A hollow screw-threaded device receives the ampoule therein. The screw-threaded device is received by the rear end of the housing. The screw-threaded device includes an exterior surface provided with a threaded surface engaging the at least one threaded portion for securing the ampoule within the housing. A medicine discharge and metering device for metering and discharging the contents of the ampoule is received within the screw-threaded device and is movable in a direction of a longitudinal axis thereof. Subsequent to administering a dosage from the ampoule, the medicine discharge and metering device enables the ampoule to move rearwardly in a direction of a longitudinal axis of the housing to an extent sufficient to release the ampoule from engagement with the ampoule fitting. The ampoule, the screw-threaded device, and the discharge and metering device are thereby permitted to swing outwardly through the slotted housing, whereby the screw-threaded device is disengaged from the at least one threaded portion, thereby enabling the screw-threaded device and the discharging and metering device to move rearwardly and to return to a starting position within the housing where the screw-threaded device can receive a new ampoule through the housing.

20 Claims, 2 Drawing Sheets

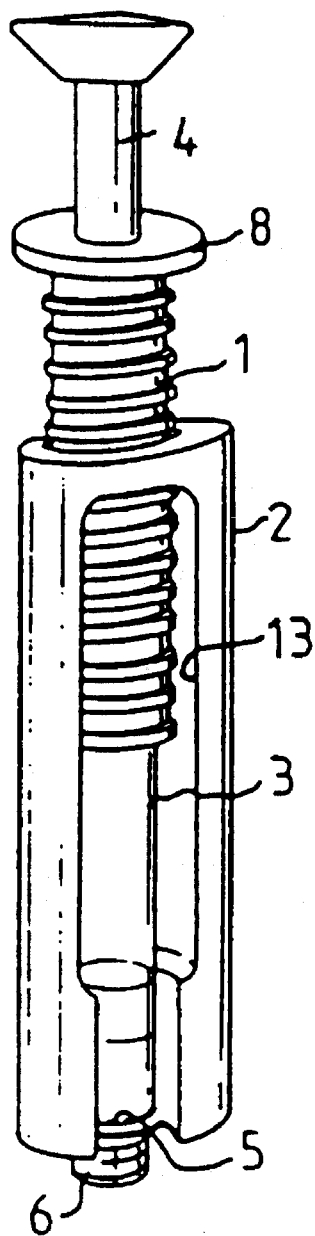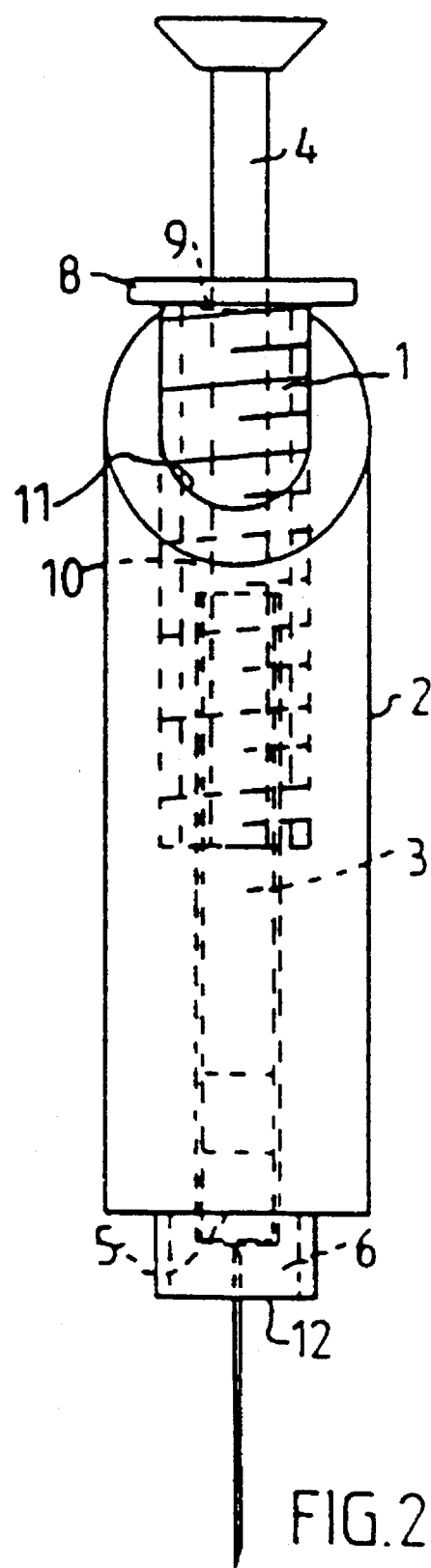

MEDICINE DISPENSING DEVICE

FIELD OF THE INVENTION

The present invention relates to a device for dispensing liquid substances in metered quantities from a container. The device includes a mechanism by means of which, after administering the contents of the container, the device can be easily returned to its original state, in which it is able to receive a further container and to dispense measured quantities of medicine therefrom. The invention particularly relates to the dispensing of medicines from a dosage cartridge or ampoule.

According to another aspect, the invention further relates to an arrangement by means of which the dispenser can be returned to its original operative state.

BACKGROUND OF THE INVENTION

One problem with known devices used to administer measured quantities of medicine, in other words dosages, such as hypodermic syringes, in particular, and also devices used to administer medicines in a pulverulent or viscous dosage form, is that they lack means which will ensure that the dispensing device can be returned quickly to its original state so that a new dosage ampoule can be fitted into the device.

The concept of the present invention can be readily applied to different known kinds of medicine dispensing devices which include a screw mechanism for reconstituting and/or metering and administering the content of a prefilled ampoule. Dispensers of this kind are well known in the art; see, for instance, U.S. Pat. No. 4,592,745.

Swedish patent specifications SE,B,465065 and SE,B, 464797 (corresponding to EP,B,298067) describe dispensers in the form of hypodermic syringes which include a screw mechanism for displacing a plunger in a prefilled cylinder.

These specifications disclose how dual-chamber ampoules can be reconstituted by rotating the screw. Dispensing and administering of the medicine is then effected with the aid of an arrangement which is activated by means of an operating lever.

In order to return a syringe of this kind to its original state and therewith enable a fresh ampoule to be fitted and reconstituted and its contents dispensed, it is necessary to withdraw the screw mechanism manually back to its starting position. This is a time consuming task and may easily be neglected, which may result in damage to the screw mechanism or in an impairment in the metering accuracy of the dispenser.

Although this problem can be overcome by constructing the dispenser, or syringe, for one-time-use only, with the intention of discarding the dispenser after having emptied the ampoule with the plunger located in its forward position, this solution is not a desirable solution, mainly for material handling reasons.

Consequently, there is a need for a dispenser which includes a simple arrangement by means of which those components of the dispenser which have been active in reconstituting and/or dispensing a measured quantity of medicine, or dose, can be quickly returned to their respective starting positions after emptying the ampoule. This applies in particular to the type of hypodermic needles described above, such needles being widely used within the art.

It is particularly desirable to provide an arrangement by means of which a screw-threaded actuator or like devices, such as the screw described above for instance, is returned quickly to its starting position in which the dispenser, or syringe, can be fitted with a fresh ampoule.

Swedish published specification 379089 and FR,A1, 2613789 teach a number of technical solutions to the problem of moving such screw-like devices quickly with the intention of releasing or securing the devices without coming into contact with the screw threads thereof.

None of these publications, however, gives an indication as to how a screw-threaded actuator intended for dispensing a metered quantity of medicine from an ampoule or similar container can be returned to its original position for administering a new dosage.

SUMMARY OF THE INVENTION

The above described problems and others are solved by the present invention, which provides a medicine dispensing device which includes an arrangement by means of which the screw-threaded actuator can be reset quickly and readily for renewed administration of a medicine dosage.

The medicine dispenser comprises generally a slotted housing which is constructed to receive a dosage ampoule and which includes at its forward end a dosage ampoule fitting and a dispensing conduit connected thereto. Mounted at the rear end of the housing is a screw-like device which functions to secure the ampoule in the fitting and which is connected to a dosage dispensing and discharging device.

According to the invention, the dispensing device is constructed so that the ampoule and the dosage discharging and metering device can be swung radially out from the housing through the slotted region thereof in a given state of the dispenser. By this is meant that after discharging and metering the content of the ampoule, the screw device can be released from the housing by swinging the device radially about its long axis, therewith enabling the ampoule to be removed radially from the dispenser housing.

As the screw-threaded discharging device is screwed down it assists in securing the ampoule in the housing, and may also contribute towards reconstituting the ampoule content, for instance by including a known mechanism for reconstituting the content of a multi-chamber ampoule (see for instance EP,B,298067). The discharging and metering device may include a plurality of mechanisms that are well known to the person skilled in this art. For instance, the invention may include mechanisms which are able to reconstitute the content of a multi-chamber ampoule and divide the ampoule into different, adjustable dosages, and to discharge the ampoule content from the dispenser. In its simplest form, the discharging and metering device may comprise an axially movable plunger rod connected to the screw-threaded device. The ampoule may consist of one or more chambers of which one may contain a reconstitutable medicine in powder form and may also include displaceable plungers which are actuable by component parts of the discharge device.

It lies within the general purviews of the invention to provide a number of different discharge devices and ampoules of alternative embodiments, according to the type of dispensing or metering desired.

The dosage ampoule is accommodated in a space provided in the housing to this end. As before mentioned, the discharge device includes a screw-threaded device which can be screwed into the rear opening of the housing. The opening has at least one screw-threaded part. The ampoule is guided axially into a fitting provided adjacent the front opening of the housing, as the screw-threaded device is screwed into the rear opening.

The ampoule can then be reconstituted and dosages for administration prepared, with the aid of the various component parts of the discharge device, in a known manner.

The arrangement is such that the ampoule is able to move axially in the hollow holder when empty and, consequently, sufficient axial space is obtainable for the empty ampoule and the screw-threaded device to be swung away from the housing and released. This axial movement of the ampoule in the container also enables the screw-like discharge device to be removed from the holder. To this end, the screw-threaded device is configured so that the weight of the ampoule will cause the ampoule to fall back axially within the device through a distance sufficient to enable the ampoule to be released from the securing device and to enable the screw-threaded device to be released from the holder. The loosened screw-threaded device can now be moved free from the screw-threaded part or parts of the opening, by swinging the device radially about its long axis, and then returning the device to its original position for fitting and dissections charging of a new ampoule. The consumed dosage ampoule can be removed radially and replaced.

The screw-threaded device with connected discharging and metering devices can be released from the screw-threaded part or parts of the opening by swinging the device radially and by withdrawing the devices beyond the screw-threaded section or sections to their starting position for receiving a new dosage ampoule. The screw-threaded device and discharging and metering devices are constructed to this end in a manner described herebelow with reference to a preferred embodiment of the invention.

BRIEF DESCRIPTION OF THE DRAWINGS

So that the invention will be more readily understood and further features thereof made apparent, the invention will now be described with reference to an exemplifying embodiment thereof and also with reference to the accompanying drawings, in which:

FIG. 1 illustrates a suitable exemplifying embodiment of the inventive medicine dispensing device;

FIG. 2 is a sectional view of the device shown in FIG. 1;

DETAILED DESCRIPTION PREFERRED EMBODIMENTS

According to one particularly preferred embodiment, shown in FIGS. 1 and 2, the screw-threaded device with connected discharging and metering devices is comprised of a screw 1 and a dispensing piston rod 4 connected thereto.

Figure 3A:
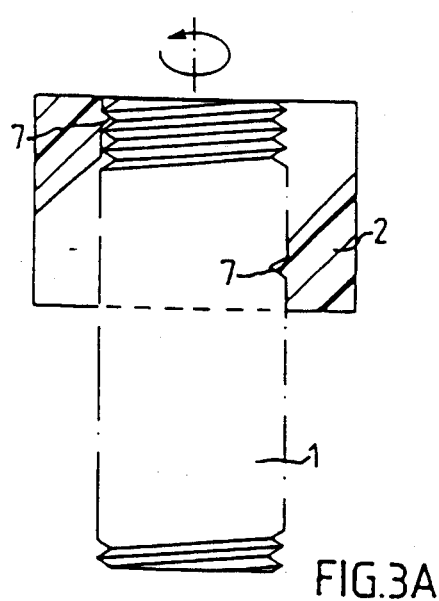
FIG. 3A is a principle sectional view of a screw-threaded device and slotted housing having two screw-threaded parts, and shows the screw-threaded device in its starting position.

When inserting a dosage ampoule 3, the screw is screwed into the hollow and slotted housing 2. The housing 2 is provided in its rear opening 11 with at least one screw-threaded part 7 (see FIG. 3A. The ampoule is guided into a fitting in the forward end 12 of the housing as the screw is turned in the screw thread. The fitting has the form of an ampoule securing recess 5. As will be seen from the drawings, the housing is slotted so as to enable the ampoule and the screw-threaded device to be swung outwardly therefrom.

In other embodiments of the invention, the screw may be caused to coact with a plunger rod of known construction (not shown) in a manner to result in reconstitution of the content of a multi-chamber ampoule and to dispense metered dosages of the ampoule content.

The dosage ampoule is preferably cylindrical and may be configured in a number of different ways. For instance, the ampoule may include one or several chambers and may optionally include displaceable plungers capable of being activated by means of the inventive discharging mechanism.

When the screw 1 has been screwed down to its limit, the ampoule contents may be discharged through a cannula or injection needle attached to the attachment device 6, by moving the plunger rod 4.

Figure 3B:
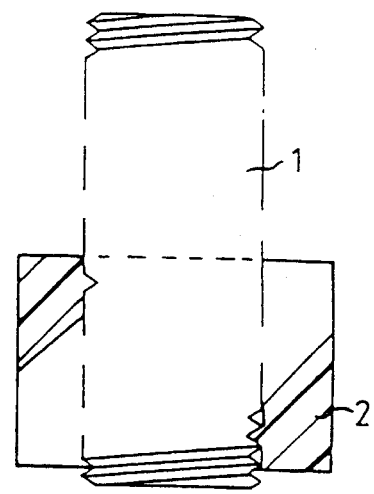
FIG. 3B is a principle, sectional view corresponding to the view shown in FIG. 3A, with the screw-threaded device in its bottom position.
Figure 3C:
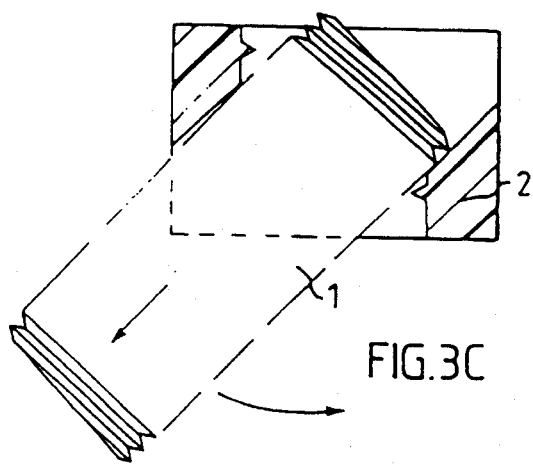
FIG. 3C is a principle, sectional view corresponding to the views of FIG. 3A and 3B, and shows the screw-threaded device swung radially out of the housing through a slotted region thereof, and withdrawn beyond the screw-threaded parts, back to its starting position.

The screw is returned to its starting position by tipping the whole of the dispensing device backwards, whereupon the ampoule is able to fall back axially through a hollow space 10 provided in the screw, so as to loosen the ampoule from the recess 5 and also from the housing. The plunger rod returns to its starting position under its own weight. The screw is loosened from the screw-threaded parts 7 by rotating the screw radially out of contact with said parts(s) 7 and returning the screw to its starting position in the aforedescribed manner (see FIG. 3C).

After emptying the ampoule, the plunger rod can be moved rearwardly in an axial direction through a distance corresponding to the last dosage dispensed from the ampoule, thereby further assisting the ampoule in its axial movement. Rearward movement of the plunger rod is limited by a shoulder 9. This enables the ampoule to be released from the housing through the groove and removed radially therefrom and a further ampoule to be inserted through an opening 13 in the housing periphery.

Figure 4A:
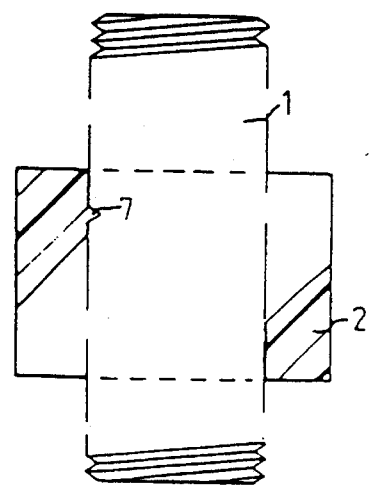
FIGS. 4A and 4B are principle, sectional views which show that the slotted housing may be provided with only one screw-threaded part and may effect the return illustrated in FIGS. 3A to 3C.
Figure 4B:
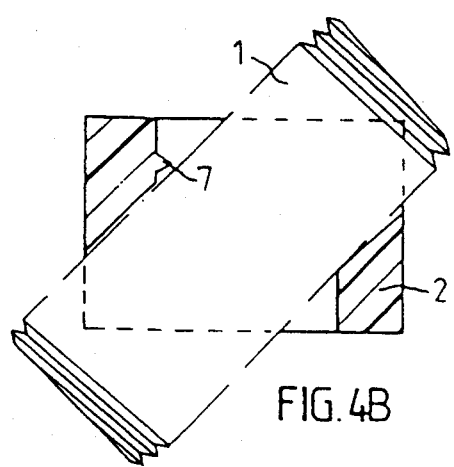

Release of the screw from the screw-threaded parts of the housing is made possible because they have been placed at a given axial distance apart, such that the distance between the parts is greater than the diameter of the screw-threaded device when the device is swung radially through the slotted region of the housing. As a result of this positioning of the screw-threaded parts, the screw-threaded device will pass free from the screw threads when the device is swung radially and drawn back to its starting position for administering a new dosage (see FIGS. 3A–3C). This return of the discharge device to its starting position can be further facilitated by bevelling the upper opening of the housing in a manner to form a space adapted for the discharge device when the device is swung radially and drawn to its starting position. The housing may also be provided with only one screw-threaded part. This screw-threaded part should then be placed at a suitable axial distance from the rear opening of the housing, so that the discharge device will pass free from engagement with the opening when rotated radially (see FIGS. 4A and 4B).

The position of respective screw-threaded parts and their configuration are adapted to each manner of construction of the holder and screw-threaded device.

Such constructional embodiments are well known to the person skilled in this art and may lead to a large number of embodiments, all of which lie within the scope of the present invention.

It will be understood that the invention is not restricted to the aforedescribed and illustrated exemplifying embodiments thereof. For instance, the aforedescribed dispensing device and mechanism can be used for rapidly returning the discharge devices of injection needles to their original positions and for replacing empty ampoules with fresh ampoules, and with other medicine dispensing devices including a screw mechanism.

The medicine dispensing device and mechanism can be adapted for use with essentially all types of medicine dispensing processes effected with the aid of different types of containers or dosage ampoules, such as parenteral, oral, nasal, rectal and ocular administration of metered dosages of medicine.

We claim:

1. A medicine dispensing device, comprising:

a housing having a slotted region, a front end including a front end opening, a rear end including a rear end opening, at least a first threaded portion provided on an inside surface of said housing in the vicinity of said rear end opening, a dosage ampoule fitting and a discharge conduit provided in the vicinity of said front end for connection with a dosage ampoule, said housing being adapted to receive said ampoule therein;

a hollow screw-threaded device also for receiving said ampoule therein, said screw-threaded device being received by said rear end opening of said housing, said screw-threaded device including on at least partially threaded outer surface engaging said first threaded, portion in the vicinity of said rear end of said housing for securing said ampoule within said housing; and a medicine discharge and metering device being received within said hollow screw-threaded device and being movable in a direction of a longitudinal axis thereof, said medicine discharge and metering device metering and discharging contents of said ampoule; and wherein subsequent to an administration of a desired dosage of the contents of said ampoule, said medicine discharge and metering device enables said ampoule to move in the direction of the longitudinal axis of said housing and rearwardly in said housing to an extent sufficient to release said ampoule from engagement with said ampoule fitting, thereby allowing said ampoule, said screw threaded device, and said discharge and metering device to swing outwardly from said housing through said slotted housing, whereby said screw-threaded device is disengaged from said at least one threaded portion, thereby enabling said screw-threaded device and said discharging and metering device to move rearwardly and to return to a starting position within said housing where said screw-threaded device is able receive a new ampoule through said slotted housing.

2. A medicine dispensing device according to claim 1, further comprising:

a plurality of threaded portions formed on an inside surface of said housing in the vicinity of said rear end, wherein said threaded portions are spaced apart at a distance which is greater than a distance between opposite points on a diagonal cross-section through said screw-threaded device.

3. A medicine dispensing device according to claim 2, wherein said rear end opening is bevelled, providing a space for said screw-threaded device to move into when said screw-threaded device is swung radially away from said housing and returned to said starting position.

4. A medicine dispensing device according to claim 2, wherein said medicine discharge and metering device comprises a plunger rod, said plunger rod being able to return to said starting position under an influence of its own weight subsequent to dispensing the contents of said ampoule, and wherein said ampoule fitting includes a recess substantially complementarily shaped to an end of said ampoule.

5. A medicine dispensing device according to claim 4, wherein said longitudinal and rearward movement of said ampoule results from the ability of said plunger rod to move freely through a distance corresponding to a volume within said ampoule of said desired dosage subsequent to said administration of said desired dosage from said ampoule.

6. A medicine dispensing device according claim 2, further comprising:

a cylindrical dosage ampoule including one or more chambers; and means in the vicinity of said front end of said housing for attaching a cannula or an injection needle to said discharge conduit, said cannula or injection needle enabling said device to be used for parenteral injection.

7. A medicine dispensing device according to claim 1, wherein said housing includes a second threaded portion positioned at a distance from said rear end of said housing so as to allow said screw-threaded device to move freely within said rear end opening and to return to said starting position when said screw-threaded device is swung radially out from said housing.

8. A medicine dispensing device according to claim 7, wherein said rear end opening is bevelled, providing a space for said screw-threaded device to move into when said screw-threaded device is swung radially away from said housing and returned to said starting position.

9. A medicine dispensing device according to claim 7, wherein said medicine discharge and metering device comprises a plunger rod, said plunger rod being able to return to said starting position under an influence of its own weight subsequent to dispensing the contents of said ampoule, and wherein said ampoule fitting includes a recess substantially complementarily shaped to an end of said ampoule.

10. A medicine dispensing device according to claim 9, wherein said longitudinal and rearward movement of said ampoule results from the ability of said plunger rod to move freely through a distance corresponding to a volume within said ampoule of said desired dosage subsequent to said administration of said desired dosage from said ampoule.

11. A medicine dispensing device according claim 7, further comprising:

a cylindrical dosage ampoule including one or more chambers; and means in the vicinity of said front end of said housing for attaching a cannula or an injection needle to said discharge conduit, said cannula or injection needle enabling said device to be used for parenteral injection.

12. A medicine dispensing device according to claim 1, wherein said rear end opening is bevelled, providing a space for said screw-threaded device to move into when said screw-threaded device is swung radially away from said housing and returned to said starting position.

13. A medicine dispensing device according to claim 12, wherein said medicine discharge and metering device comprises a plunger rod, said plunger rod being able to return to said starting position under an influence of its own weight subsequent to dispensing the contents of said ampoule, and wherein said ampoule fitting includes a recess substantially complementarily shaped to an end of said ampoule.

14. A medicine dispensing device according to claim 13, wherein said longitudinal and rearward movement of said ampoule results from the ability of said plunger rod to move freely through a distance corresponding to a volume within said ampoule of said desired dosage subsequent to said administration of said desired dosage from said ampoule.

15. A medicine dispensing device according claim 12, further comprising:

a cylindrical dosage ampoule including one or more chambers; and means in the vicinity of said front end of said housing for attaching a cannula or an injection needle to said discharge conduit, said cannula or injection needle enabling said device to be used for parenteral injection.

16. A medicine dispensing device according to claim 1, wherein said medicine discharge and metering device comprises a plunger rod, said plunger rod being able to return to said starting position under an influence of its own weight subsequent to dispensing the contents of said ampoule, and wherein said ampoule fitting includes a recess substantially complementarily shaped to an end of said ampoule.

17. A medicine dispensing device according to claim 16, wherein said longitudinal and rearward movement of said ampoule results from the ability of said plunger rod to move freely through a distance corresponding to a volume within said ampoule of said desired dosage subsequent to said administration of said desired dosage from said ampoule.

18. A medicine dispensing device according claim 17, further comprising:

a cylindrical dosage ampoule including one or more chambers; and means in the vicinity of said front end of said housing for attaching a cannula or an injection needle to said discharge conduit, said cannula or injection needle enabling said device to be used for parenteral injection.

19. A medicine dispensing device according to claim 16, further comprising:

a cylindrical dosage ampoule including one or more chambers; and means in the vicinity of said front end of said housing for attaching a cannula or an injection needle to said discharge conduit, said cannula or injection needle enabling said device to be used for parenteral injection.

20. A medicine dispensing device according to claim 1, further comprising:

a cylindrical dosage ampoule including one or more chambers; and means in the vicinity of said front end for attaching a cannula or an injection needle to said discharge conduit, said cannula or injection needle enabling said device to be used for parenteral injection.

* * * * *